(12) United States Patent
Harttig et al.

(10) Patent No.: US 9,131,886 B2
(45) Date of Patent: *Sep. 15, 2015

(54) APPARATUS FOR ACQUIRING AND ANALYZING A BLOOD SAMPLE

(71) Applicant: Roche Diagnostics Operations, Inc., Indianapolis, IN (US)

(72) Inventors: Herbert Harttig, Neustadt (DE); Jürgen Braun, Ehningen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 252 days.

This patent is subject to a terminal disclaimer.

(21) Appl. No.: 13/938,000

(22) Filed: Jul. 9, 2013

(65) Prior Publication Data

US 2014/0005510 A1  Jan. 2, 2014

Related U.S. Application Data

(63) Continuation of application No. 12/753,454, filed on Apr. 2, 2010, now Pat. No. 8,496,602.

(30) Foreign Application Priority Data

Apr. 3, 2009  (EP) .................................. 09004930

(51) Int. Cl.
*A61B 5/151* (2006.01)
*A61B 5/15* (2006.01)
(Continued)

(52) U.S. Cl.
CPC ............ *A61B 5/15128* (2013.01); *A61B 5/1411* (2013.01); *A61B 5/14532* (2013.01);
(Continued)

(58) Field of Classification Search
CPC ........... A61B 5/14532; A61B 5/15146; A61B 5/1411
See application file for complete search history.

(56) References Cited

U.S. PATENT DOCUMENTS

RE35,803 E   5/1998  Lange et al.
5,772,677 A  6/1998  Mawhirt et al.
(Continued)

FOREIGN PATENT DOCUMENTS

EP   0 565 970 B1   9/1997
EP   1 402 812 A1   3/2004
(Continued)

OTHER PUBLICATIONS

European Search Report—EP 09 00 4930, dated Jun. 25, 2009.

*Primary Examiner* — Adam J Eiseman
*Assistant Examiner* — Patrick Fernandes
(74) *Attorney, Agent, or Firm* — Bose McKinney & Evans LLP

(57) ABSTRACT

An automatic apparatus for obtaining and analyzing a blood sample contains a supply of lancets and test strips, which are located alternately on a carrier band. A lancet or alternatively a test strip may be clamped on a holder, which is mounted so it is movable. The movement controller of the holder comprises a three-dimensional control curve and a guide element, which engages at different depths in the control curve as a function of its relative position. The control curve comprises two guide paths, which run on different parallel planes. The contour of the first guide path determines the movement path of the lancet and the contour of the second guide path determines the movement path of the test strip. The test strip executes a transverse offset perpendicular to the puncture axis of the lancet.

22 Claims, 8 Drawing Sheets

(51) Int. Cl.
  *A61B 5/145* (2006.01)
  *A61B 5/157* (2006.01)
(52) U.S. Cl.
  CPC ............ *A61B5/157* (2013.01); *A61B 5/15117* (2013.01); *A61B 5/15146* (2013.01); *A61B 5/15169* (2013.01); *A61B 5/15171* (2013.01); *A61B 2562/0295* (2013.01)

(56) References Cited

U.S. PATENT DOCUMENTS

| | | |
|---|---|---|
| 5,846,096 A | 12/1998 | Ishida |
| 6,197,040 B1 | 3/2001 | LeVaughn et al. |
| 6,472,220 B1 | 10/2002 | Simons et al. |
| 7,223,276 B2 | 5/2007 | List et al. |
| 7,481,777 B2 | 1/2009 | Chan et al. |
| 2004/0138588 A1 | 7/2004 | Saikley et al. |
| 2005/0234494 A1 | 10/2005 | Conway et al. |
| 2006/0173380 A1 | 8/2006 | Hoenes et al. |
| 2006/0247555 A1 | 11/2006 | Harttig |
| 2007/0142776 A9 | 6/2007 | Kovelman et al. |
| 2008/0033469 A1 | 2/2008 | Winheim et al. |
| 2009/0287116 A1 | 11/2009 | Konya |
| 2010/0009432 A1 | 1/2010 | Lee et al. |

FOREIGN PATENT DOCUMENTS

| | | |
|---|---|---|
| EP | 1 714 613 A1 | 10/2006 |
| EP | 1 884 191 A1 | 2/2008 |
| EP | 1 992 283 A1 | 11/2008 |
| WO | WO 2008/083844 A1 | 7/2008 |

APPARATUS FOR ACQUIRING AND ANALYZING A BLOOD SAMPLE

RELATED APPLICATIONS

This is a continuation of U.S. patent application Ser. No. 12/753,454, filed Apr. 2, 2010, which claims priority to EP09004930.5, filed Apr. 3, 2009, both of which are hereby incorporated by reference in their entireties.

BACKGROUND

The invention relates to an apparatus for acquiring and analyzing a blood sample.

Diabetics are instructed that it is important to regularly self-check their blood sugar level. For this purpose, the tip of a lancet must be stuck into the skin of a body part, preferably into the fingertip. A drop of blood exits from the small wound, which is taken up by an analysis element such as a test strip, for example, and subsequently supplied to analysis.

Small automatic handheld devices having an integrated measuring unit and lancets implemented as disposable articles are known in the art. One current development is directed toward an electrically driven apparatus, in which not only the piercing and receiving of a blood sample, but rather also the subsequent analysis up to the output of a measurement result run completely automatically. A supply of disposable lancet test strips is stored in a magazine, so that a number of tests can be performed before the consumable material must be replaced. The advantage of a highly developed apparatus of this type is obvious: while the patient earlier had to carry a piercing aid having a sufficient quantity of lancets and test strips as well as a measuring apparatus and had to handle each of them separately, now a single apparatus, which is conceivably simple to operate, is sufficient to be equipped for monitoring the blood sugar level for days.

It is clear that the design of an apparatus which not only acquires the blood sample, but rather also automatically analyzes it, places a great demand on the designer if all conditions which are currently placed on such a apparatus are to be met. These conditions include, in particular, simple and comfortable operation, ultrahigh reliability, small and light construction, and design simplicity, so that the manufacturing costs may remain acceptable for a mass-produced article. In contrast to simple puncture aids, in which the piercing drive must only drive the lancet, a fully automatic blood sugar test apparatus requires a drive mechanism, which not only drives the lancet, but rather also guides the analysis element to the body part in which piercing was just performed, and then supplies the blood sample to the analysis in a further step. The particular problem is that it makes little sense to move the analysis element in the same manner and on the same path as the lancet, because the analysis element is completely different in form and function from the lancet. A complete movement controller must thus be provided, which is capable of guiding the analysis element to the fixed body part so that it comes into contact with the body part at a different point than the lancet did previously.

Publication No. WO 2008/138 455 A1 describes a puncture system having a device housing, a housing opening for applying a body part, a number of lancets for generating a puncture wound in the body part, sample receiving apparatuses for receiving a bodily fluid sample from the puncture wound, a drive which moves the lancet to generate a puncture wound and subsequently moves a sample receiving apparatus to the puncture wound, and having a coupling part, which couples a lancet and subsequently a sample receiving apparatus to the piercing drive. The system also has a movement controller, which causes the coupling part to reach a final position during a sample receiving movement which is laterally displaced relative to the final position which the coupling part reaches during a puncture movement. Lancets and sample receiving apparatuses are located on a carrier band, which is transported transversely through a gap of the coupling part. The carrier band is bent in the longitudinal direction during the puncture movement, so that the tip of the lancet lifts off of the carrier band. When a sample is taken up, the carrier band is also folded in its longitudinal direction, so that the puncture wound is contacted flatly by the bent-over carrier band and the sample receiving apparatus located thereon, namely a test panel. The movement controller causes a lateral displacement transversely to the puncture direction, so that the puncture wound is contacted flatly by the bent-over test panel. The movement controller accordingly comprises a curved controller having a first control curve for a puncture movement and a second control curve for a sample receiving movement. These control curves run in a guide element, which extends in the puncture direction. A resilient shunt of the control curves determines which one of the control curves a control curve rider travels down. To change over between puncture movement and sample receiving movement, the control curve rider must pass below the shunt, the shunt briefly being raised. This requires force, which must be applied by the piercing drive and which impairs the smooth running and steadiness of the kinematics. Furthermore, it is disadvantageous that the shunt is a component to be produced separately and inserted into the movement controller, which causes additional manufacturing and assembly costs.

SUMMARY OF THE INVENTION

The present invention improves and simplifies a movement controller for the lancet and the analysis element. This is achieved in exemplary embodiments by a three-dimensional control curve having at least two differently contoured guide paths, which lie on different planes, which run parallel to the puncture axis of the lancet and to the direction of the transverse offset of the analysis element, the contour of the first guide path determining the movement path of the lancet for a piercing and the contour of the second guide path determining the movement path of the analysis element for taking up the blood sample, and by at least one guide element, which, depending on its relative position, engages at different depths in the control curve as a function in order to travel down the contours of the guide paths.

The lancet and the analysis element may be coupled either alternately, i.e., one after the other, and also both simultaneously to the holder, for example, in the form of an integrated disposable. In the latter case, it must be ensured that during the movement of the holder provided for receiving the blood sample, the lancet does not also come into contact with the piercing point once again.

According to one embodiment, the control curve is a spatial formation which extends in all three spatial axes. The guide paths lie on different planes, i.e., they are staggered in depth. The guide path of the first plane defines the movement path of the holder for the lancet and the guide path of the second plane determines the movement path of the holder for the analysis element. The desired transverse offset (transverse offset movement) of the analysis element relative to the puncture axis of the lancet can be achieved in that the guide paths lying on various planes are contoured differently. The various planes of the guide paths run parallel to the puncture axis and parallel to the direction of the transverse offset.

The control curve controls the movement of the holder in a first axis, which runs parallel to the puncture axis, and in a second axis perpendicular thereto, which runs parallel to the direction of the transverse offset of the analysis element. If one places the three-dimensional control curve in an orthogonal coordinate system, the contours of the guide paths predetermine the movements of the holder in the x and y directions. The dimension of the control curve leading into the spatial depth (z axis) has no influence on the movement paths of the lancet and the analysis element, but rather is solely used to select which of the guide paths is to be traveled down. For this purpose, it is necessary for the guide element to engage at different depths in the control curve, in order to always remain in contact with the control curve.

The various guide paths whose contour the guide element travels down may be selected easily in that a transition is made from one plane to the other. Solely because the guide element starts at specific different positions, it changes back and forth between the various guide paths. This changeover between the various guide paths is achieved without a further component such as a shunt. The entire movement controller is thus reduced to two elements working together, namely the three-dimensional control curve and the guide element sliding therein.

One of the guide paths has a substantially linear contour for the movement controller of the lancet, which shoots out along the puncture axis and is immediately retracted on the same route. This contour determines the movement path of the holder and thus also the lancet coupled to the holder, when it executes a piercing.

The desired transverse offset of the analysis element relative to the puncture axis can be generated in that the associated guide path has a curved contour. The endpoint of the curvature determines the amount of the transverse offset and the radius determines the velocity at which the analysis element is moved transversely to the puncture axis. In practice, a contour of the guide path for the analysis element which is composed of linear and curved sections has proven itself. It is thus possible to first guide the analysis element on a curved movement path having a movement component perpendicular to the puncture axis and subsequently to guide it simply parallel to the puncture axis upon the approach to the skin surface.

In order that the guide element passes from one guide path to the other easily, which is accompanied by a change of the plane, the guide profile advantageously comprises at least one ramp-like transition path, which connects the guide paths lying on different planes. The guide element can travel from one plane to the other on such a ramp, without having to overcome a step. This does not preclude, of course, that the guide element also changes the guide path and thus the plane inside the control curve in another way, for example, by "dropping down" or "jumping up" a step. A ramp-like transition path has the advantage, however, that the guide element can slide on a continuous path from plane to plane.

In one embodiment, the control curve is permanently connected to the holder and the guide element is mounted fixed relative to the housing. In this case, the guide element acts like a bearing on which the control curve slides.

In order to allow the guide element to engage at different depths in the control curve as a function of its position, so that it can travel down the contours of the guide paths, the guide element is advantageously implemented as a guide cylinder, which is mounted so it is displaceable in the axial direction. A spring acting in the axial direction on the guide cylinder ensures that the guide cylinder is pressed onto the guide paths of the control curve and kept engaged. Such an elastically mounted guide element thus compensates for the spacing between the planes on which guide paths are located. Alternatively, the guide element can be implemented as telescopic and, for example, comprise two, preferably cylindrical parts which are displaceable to one another in the axial direction.

In an expedient and advantageous embodiment, the holder for the lancet and/or the analysis element has a main body in the form of a rectangular cuboid, which extends parallel to the puncture axis, and the control curve is implemented in a long side wall of the holder. For example, the profile of the control curve can be integrally molded in the side wall of the holder.

The guide element engaging in the control curve preferably extends transversely to the puncture axis and thus perpendicularly to the planes of the guide paths.

Because the holder is to move back and forth parallel to the puncture axis above all, a control curve is preferably implemented on each of two diametrically opposite side walls of the holder, in each of which a fixed guide element engages. The control curves and guide elements are implemented as mirror images and may be located diametrically opposite one another. The holder is then mounted between the two fixed guide elements. Lateral tilting of the holder is thus prevented.

The holder must be coupled to the piercing drive so that it can execute not only a movement parallel to the puncture axis, but rather also the desired transverse offset perpendicular to the puncture axis. This can be implemented, for example, in that the holder is connected to the piercing drive via an articulated coupling, which permits a tilting movement of the holder around an axis transverse to the puncture axis. Such an articulated coupling preferably comprises a plug receptacle for a coupling pin of the piercing drive. The movable mounting of the coupling pin in the plug receptacle can be implemented by a leaf spring, which is seated in the plug receptacle and presses laterally against the coupling pin.

Alternatively, the two mirror-image control curves and the associated guide elements may be located offset to one another in the direction of the puncture axis. In this case, the holder can simply be raised upward or lowered downward parallel to the puncture axis, in order to cause the desired transverse offset of the analysis element. Tilting of the holder around an axis transverse to the puncture axis can thus be avoided. Of course, the holder must be mounted correspondingly so it is smooth-running. The design of the guide paths of the control curves is to be adapted accordingly.

If the holder carries a clamping device on its front end in the puncture direction, it can, optionally, be used to clamp on a disposable lancet or a disposable analysis element. After the puncture, the lancet can be replaced with an analysis element. If the analysis element has also performed its job, a lancet can be clamped on again. Fundamentally, however, it is also possible to clamp on a lancet and an analysis element simultaneously, for example, if an integrated disposable is used.

Disposable lancets and analysis elements in the form of disposable test strips are preferably alternately located on a carrier band, which is drawn step-by-step transversely to the puncture direction through the clamping device of the holder. The carrier band also ensures the further transport of the blood sample taken up by the test strip to an analysis unit, which measures the blood sugar content.

In an advantageous and expedient refinement, a removable replaceable cassette, which contains a supply of disposable lancets and disposable test strips, is inserted into the housing. If the lancets and the test strips are located alternately on a carrier band, the replaceable cassette expediently contains a supply coil and a winding coil. The carrier band having unused lancets and test strips can be unwound from the supply coil and transported to the clamping device of the holder.

After the single use, the lancets and/or test strips are transported away from the holder again using the carrier band. The carrier band having the used lancets and test strips is then wound onto the winding coil. If the supply of lancets and test strips has been used up, the user can easily and comfortably remove the entire replaceable cassette from the apparatus and replace it with a new one.

An embodiment in which the holder is mounted on the replaceable cassette is particularly preferred. Fundamentally, the holder can also be mounted so it is movable in the housing independently of the replaceable cassette; however, the mounting on or in the replaceable cassette has the advantage that the unavoidable play between replaceable cassette and housing has no negative influence on the precision of the movement sequences when coupling and decoupling the lancets and/or analysis elements on or from the holder, respectively. A further advantage is that the holder can be replaced together with the replaceable cassette and thus the insertion of the carrier band into the clamping device of the holder can be performed with very high reliability during production.

The holder can be located between the supply coil and the winding coil so that the carrier band is transported transversely to the puncture direction through the area of the clamping device of the holder. The diameter of the two coils can thus be used simultaneously for the main extension direction of the holder, so that the replaceable cassette as a whole has very compact dimensions.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
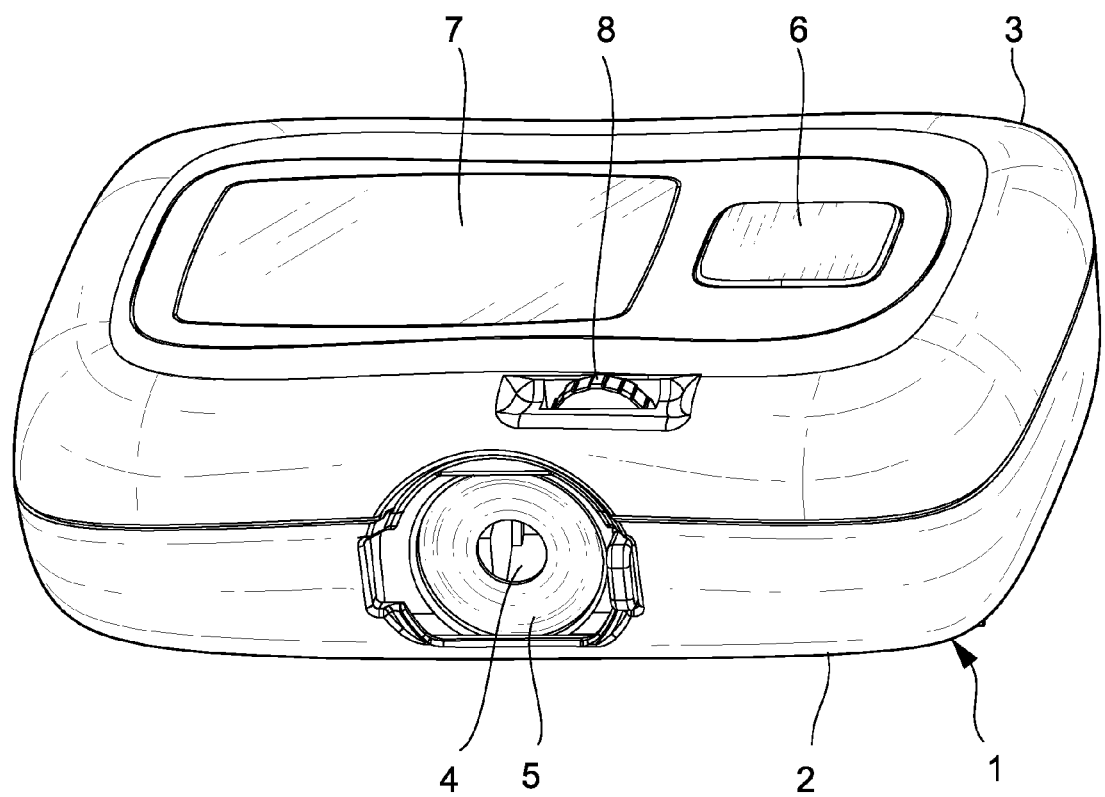
FIG. 1 is a perspective view of a complete apparatus for obtaining and analyzing a blood sample.

The apparatus shown in FIG. 1 for obtaining and analyzing a blood sample has a flat rectangular housing 1 having rounded corners. The housing 1 is manufactured from plastic and comprises a housing bottom part 2 and a housing cover 3. A round opening 4 is provided on the front side, which is delimited by a fixing ring 5. The fixing ring 5 is shaped so that the tip of a finger can be pressed against it. In this way, the fingertip from which a blood sample is to be taken may be fixed on the apparatus.

An operating panel 6, which comprises buttons for operating the apparatus, is provided on the housing cover 3. A large-area display 7 is located adjacent thereto, on which the result of the blood sugar test can be read. A setting wheel 8 is used for adjusting the fixing ring 5 in order to adapt the piercing depth optimally to the shape of the finger.

A piercing device having a lancet 9 (not visible here) is concealed behind the opening 4, which shoots out of the opening 4 in order to pierce the skin of the finger pressed against a fixing device provided as a fixing ring 5 and subsequently retracts again immediately. Subsequently, an analysis element can be led to the fixed finger on the same route, in order to take up a blood drop exiting from the puncture wound, which is then supplied to an automatic analysis in the interior of the apparatus.

Figure 2:
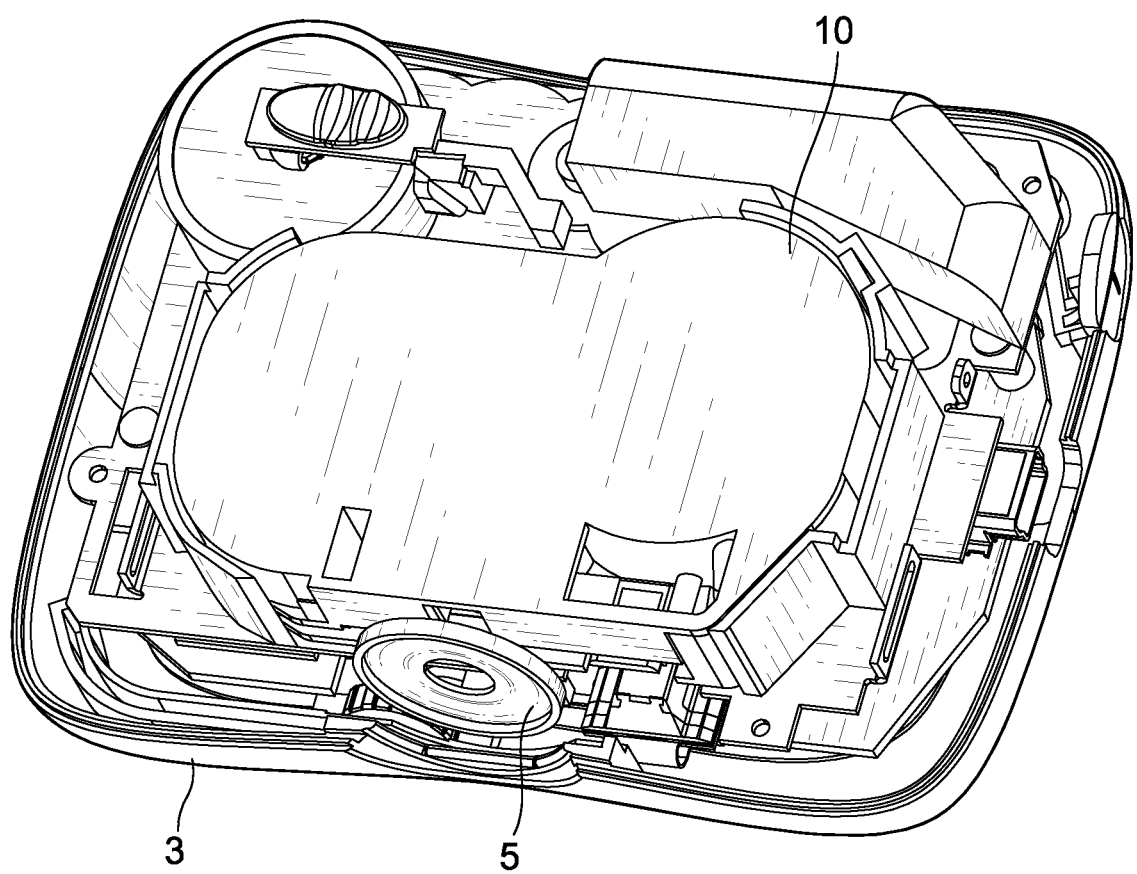
FIG. 2 is a perspective view of the apparatus from FIG. 1 shown from below, with the bottom housing part removed.

In FIG. 2, the apparatus is turned over and the housing bottom part 2 is removed, so that only the edge of the housing cover 3 is still visible. A replaceable cassette 10 contains a supply of disposable lancets, which are intended for one-time use. The replaceable cassette 10 also contains a supply of analysis elements.

Figure 3:
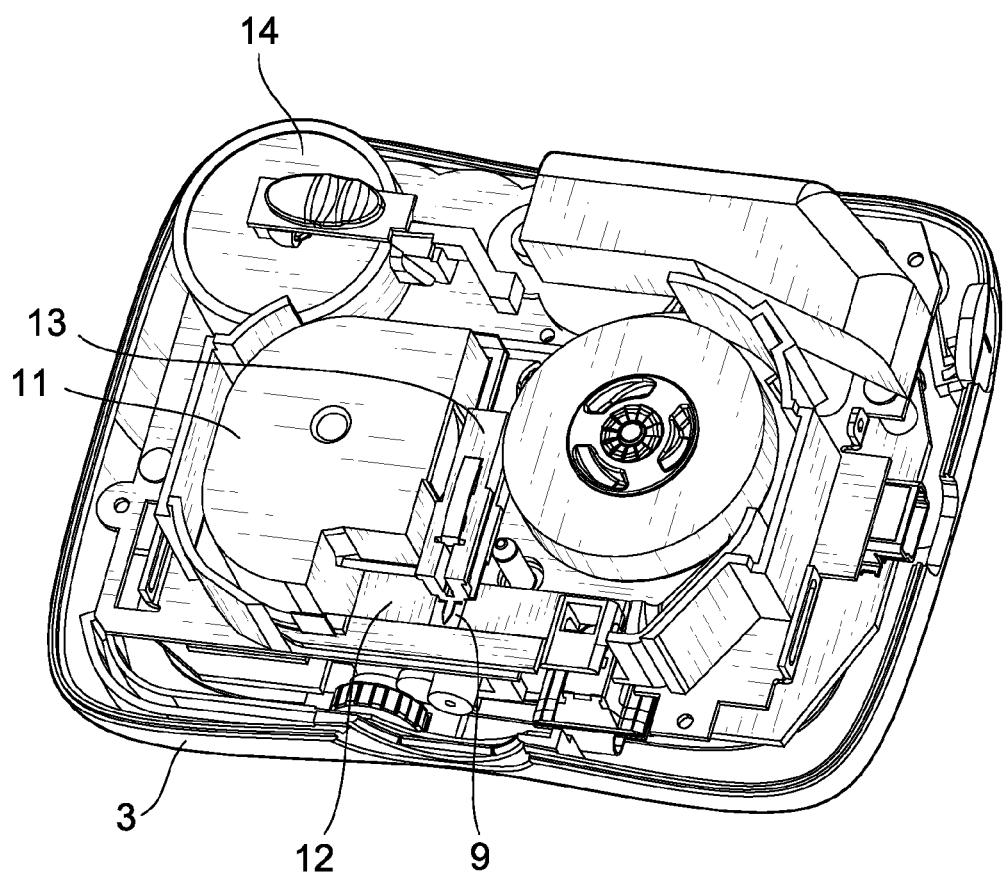
FIG. 3 is a perspective view of the apparatus from FIG. 1 after removal of the base of the replaceable cassette.

In FIG. 3, the cover of the replaceable cassette 10 has been removed, so that the view of a supply magazine 11 is exposed. The supply magazine 11 contains a carrier band 12, on which disposable lancets and analysis elements are located alternately one behind another. A holder 13 is located in the replaceable cassette 10 adjacent to the supply magazine 11, to which either a lancet or an analysis element can be coupled. The holder 13 is mounted so that it is movable on the base of the replaceable cassette 10.

Figure 4:
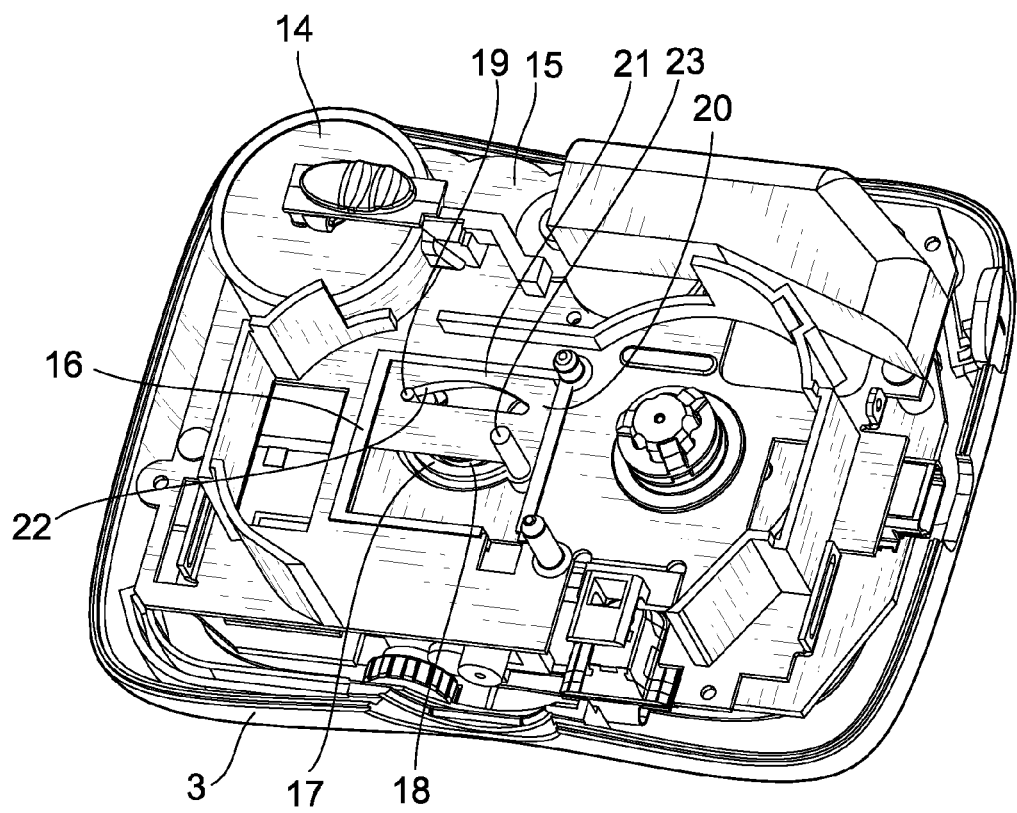
FIG. 4 is a perspective view of the apparatus from FIG. 1 after complete removal of the replaceable cassette.

In FIG. 4, the replaceable cassette 10 is removed together with the holder 13 so that the drive mechanism is visible. It essentially comprises an electric motor 14, a transfer gear 15, and a piercing drive 16. The piercing drive 16 comprises a rotor 17, which is set into rapid rotation by a tensioned coil spring 18. The rotation of the rotor 17 is transmitted to a sliding part 20 via a tappet pin 19. The tappet pin 19 runs in a recess 21, which is implemented in the form of a circular section and forms a control curve 22. The sliding part 20 carries a coupling pin 23, which engages from below in the holder 13 (cf. FIG. 3) and transmits the movement of the sliding part 20 to the holder 13 in this way.

The sliding part 20 converts the rotational movement of the rotor 17 into a linear movement of the coupling pin 23 parallel to the puncture axis. After approximately half a rotation of the rotor 17, the tappet pin 19 has traveled down the control curve 22 and reached its final position in the recess 21. In order to tension the coiled spring 18 again, the rotor 17 must be rotated in the opposing direction. For this purpose, the rotor 17 is coupled via a freewheel to the transfer gear 15. The piercing drive is thus only tensioned using the electric motor 14, while the actual drive of the lancet 9 (cf., FIG. 1) is performed by the force of the coiled spring 18.

The recess 21 can alternatively also be implemented so that the tappet pin 19 travels down a first control curve when the rotor 17 is set into a rapid rotation by the tensioned coiled spring 18, and travels down a second other control curve (not shown here) when the rotor 17 executes a rotation in the opposite direction by the electric-motor drive upon tensioning of the coiled spring 18. The second control curve is implemented so that the linear movement of the sliding part 20 comprises different distances in the opposing movement directions of the rotor 17. The movement path upon tensioning of the coiled spring 18 is longer than upon the rapid puncture movement.

Figure 5:
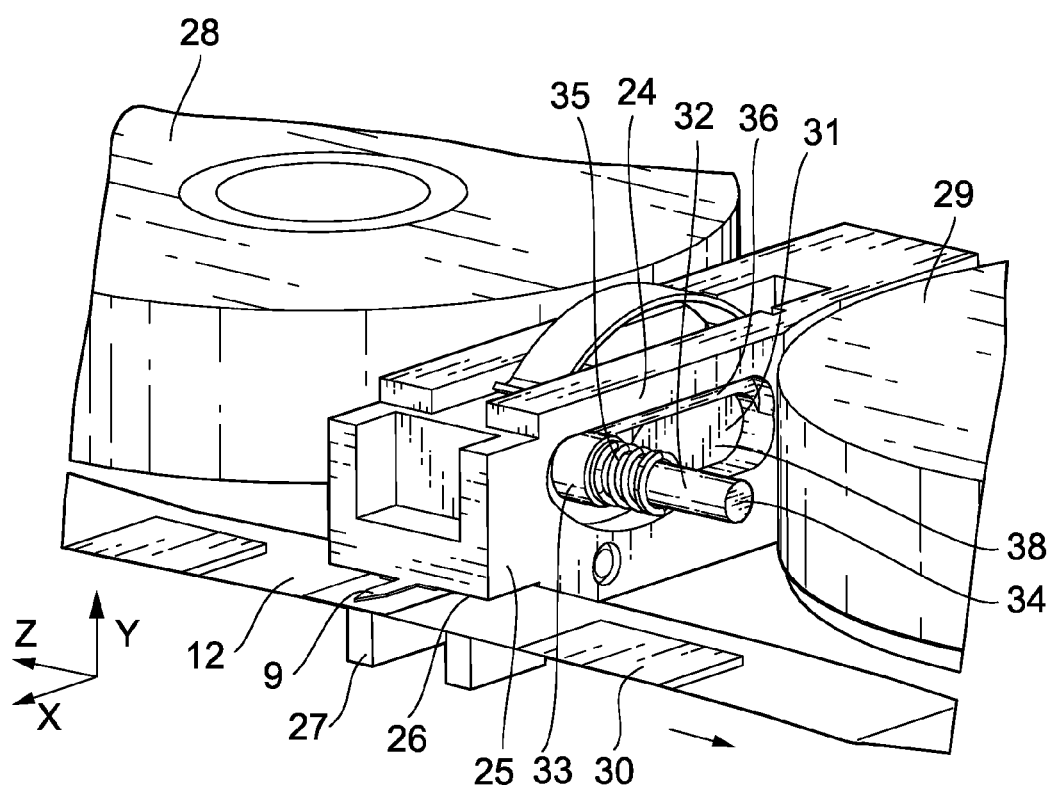
FIG. 5 is an enlarged fragmentary perspective view of the holder according to FIG. 3.

The detail enlargement of FIG. 5 shows the area around the holder 13 in detail. The holder 13 has a main body 24 in the form of a rectangular cuboid, which extends parallel to the puncture axis. A gripper 25 is installed on the forward front side, which comprises a slot 26 and a pivotable clamping jaw 27. A lancet 9 is located in particular in the slot 26 and is fixed on the gripper 25 by the clamping jaw 27. The carrier band 12 is unwound from a supply coil 28, transported transversely to the puncture axis through the slot 26, and wound on a winding coil 29. The holder 13 having gripper 25 is located in the middle between supply coil 28 and winding coil 29.

Analysis elements in the form of test strips 30 are located on the carrier band 12 in front of and behind the lancet 9. The gripper 25 can thus alternately grasp a lancet 9 or a test strip 30 and couple it on the holder 13. After the single use, the lancet 9 or the test strip 30 is transported away by the carrier band 12 and stored on the winding coil 29 at the end. The test strips 30 previously pass through an analysis unit (not shown), which measures the blood sugar content. Supply coil 28 and winding coil 29 are located in the interior of the replaceable cassette 10 (cf. FIG. 2). If the carrier band 12 has run through completely, the supply of lancets 9 and test strips 30 is exhausted. The replaceable cassette 10 can then be replaced with a new one.

The lancet 9 comprises a piece of flat steel having a sharp tip. The test strips 30 comprise a porous material, which absorbs blood especially well, and an adjoining layer made of chemicals which react differently upon contact with the blood depending on how high the blood sugar content is. This reaction can be evaluated visually or electrically, for example, and the result can be shown on the display 7 (cf. FIG. 1).

The holder 13 must execute different movements depending on whether a lancet 9 or a test strip 30 is seated in the gripper 25. While the lancet 9 is guided in a linear movement forward along the puncture axis and subsequently retracted again on the same route, a test strip 30 must be guided on an alternative movement path, which comprises a transverse offset movement perpendicular to the puncture axis of the lancet 9. This transverse offset movement runs parallel to the y axis of the coordinate system shown in FIG. 5.

The movement control of the holder 13 is performed by control curves or guide recesses, which are implemented in the long side walls of the holder 13. Only one side wall of the holder (on the right in the puncture direction) having the control curve 31 implemented therein is shown in FIG. 5. A second control curve, which is implemented in a mirror image, is arranged in the opposing side wall. Only the one control curve 31 is described in greater detail hereafter, it being clear that the second, mirror-image control curve is arranged and implemented in the same way.

A guide element 32 engages in the control curve 31. The guide element 32 extends transversely to the puncture axis, i.e., in the direction of the z axis of the coordinate system. The guide element 32 engages at different depths in the three-dimensional control curve 31 as a function of its position.

The guide element 32 is formed by a guide cylinder 33, which is seated on the free end of a bearing journal 34. The other end of the bearing journal 34 is mounted so it is axially displaceable in a wall (not shown here) of the replaceable cassette 10. A spring 35 acting in the axial direction, which is implemented here as a compression spring coiled around the bearing journal 34, presses the guide cylinder 33 into the control curve 31.

A second, identically implemented guide element is located on the diametrically opposite side of the holder 13 and engages (not visible in the drawing) in the second control curve on the other side (not visible) of the holder 13.

Figure 6A:
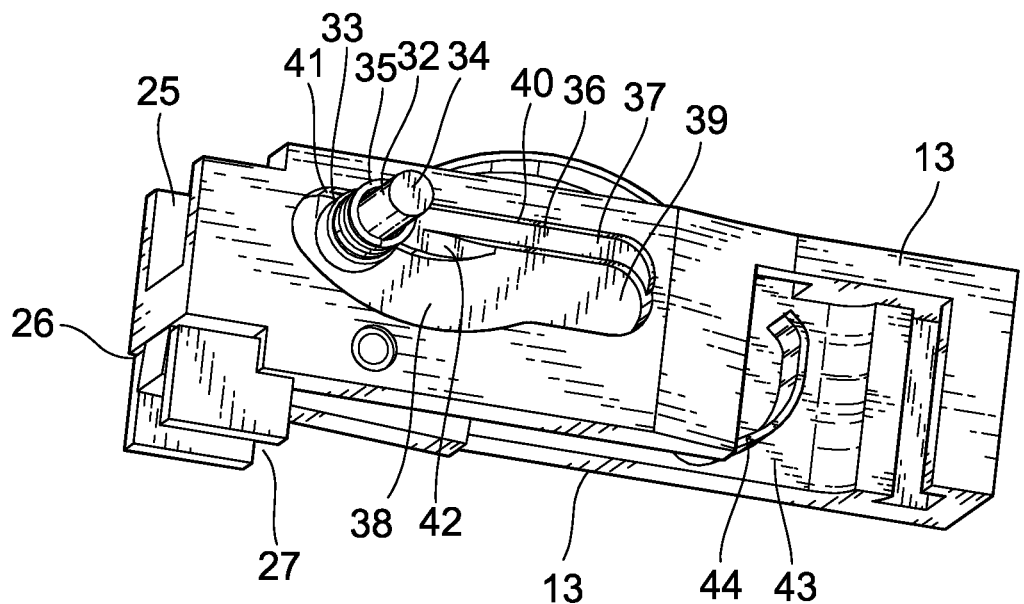
FIG. 6a is a perspective view of the holder having a spring-loaded guide element, shown diagonally from below.
Figure 6B:
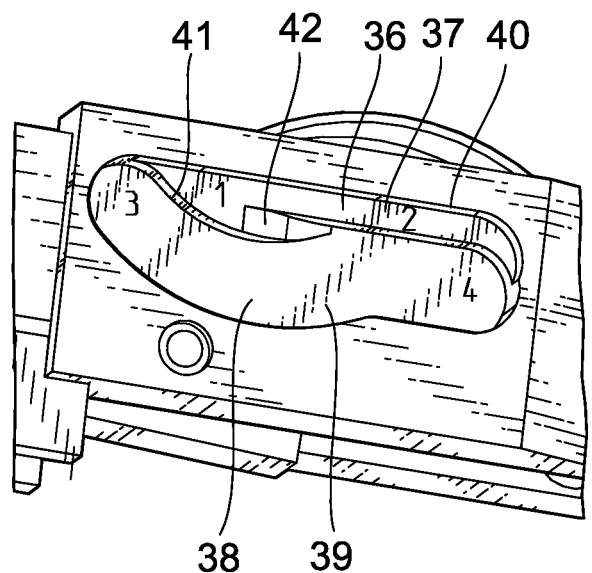
FIG. 6b is an enlarged fragmentary perspective view of the control curve of the holder.

The three-dimensional implementation of the control curve 31 can be seen clearly in FIGS. 6a and 6b. The control curve 31 comprises a first guide path 36, whose base runs on a first plane 37, and a second guide path 38, whose base runs on a second plane 39. The planes 37 and 39 are parallel to one another and extend both parallel to the puncture axis and also parallel to the direction of the transverse offset movement, i.e., the planes 37 and 39 thus run parallel to the plane spanned by the x axis and y axis. Starting from the lateral surface of the holder 13, the guide paths 36 and 38 thus lie at different depths (z axis).

The first guide path 36 has an essentially linear contour 40 and thus determines the linear movement path of the lancet 13. In contrast, the second guide path 38 has a curved contour 41 and determines the movement path of a test strip 30. The upwardly running curve of the contour 41 causes the desired transverse offset movement of the analysis element in the y direction relative to the puncture axis. A ramp-like transition path 42 is provided between the first guide path 36 and the second guide path 38. This allows the guide cylinder 33 to slide from the second guide path 38 onto the first guide path 36, although these paths lie on the different planes 37 and 39, respectively. The coiled spring 35 ensures that the guide cylinder 33 is always engaged with one guide path 36 or 38 or the inclined transition path 42. The guide element 32 can thus travel back and forth in the x direction and up and down in the y direction inside the control curve 31 and change from the first guide path 36 to the second guide path 38 without disengaging.

The relative movement between holder 13 and guide element 32 corresponds to the movement in the x and y directions executed by the holder 13 and thus the lancet 9 or a test strip 30. In contrast, the additional movement of the guide cylinder 33 in the z direction has no influence on the movement profile of the holder 13. The third dimension of the control curve 31 is exclusively used for changing over from the first guide path 36 to the second guide path 38, this changeover occurring automatically as a function of the position of the guide element 32.

A recess is provided on the bottom side of the holder 13, which is implemented as a plug receptacle 43. When the holder 13 is inserted into the apparatus (cf. FIG. 3), the coupling pin 23 of the sliding part 20 engages in the plug receptacle 43 from below. A curved leaf spring 44 protrudes into the plug receptacle 43 so that it presses against the coupling pin 23 from the side. In this way, the holder 13 is connected to the piercing drive via an articulated coupling, so that the holder 13 can execute a pivot movement around a rotational axis transverse to the puncture axis (i.e., parallel to the z axis in FIG. 5). This tilting movement of the holder 13 allows the transverse offset movement of the front end of the holder 13 perpendicular to the puncture axis, when a test strip 30 is seated in a gripper 25.

Four positions of the guide element 32 in the control curve 31 are marked in FIG. 6b by the consecutive numbers (1), (2), (3), and (4).

Position (1) is the starting position, in which the piercing drive is located in the idle position, i.e., the coiled spring 18 is tensioned and a fresh lancet 9 is seated in the gripper 25. After the user triggers the puncture, the holder 13 is driven forward (to the left in FIG. 7, in the x direction in FIG. 5). The guide cylinder 33 travels down the linear contour 40 of the first guide path 36, which is converted into a linear movement of the lancet 9 along the puncture axis.

The forward movement of the lancet is stopped when the guide cylinder 33 has reached the reversal position (2). From there on, the holder 13 is accelerated in the reverse direction. This is the rapid retraction movement of the lancet 9.

The retraction movement of the lancet 9 runs beyond the idle position (1), and the guide cylinder 33 reaches the position (3). At this point, the guide cylinder 33 leaves the contact with the first guide path 36, which ended briefly before. Under the effect of the coiled spring 35, the guide cylinder 33 "drops down" to the lower-lying second plane 39 and thus reaches the second guide path 38. Shortly before or shortly after this moment, the lancet 9 is removed from the gripper 25 and replaced with an unused test strip 30.

The device is now ready to take up the drop of blood exiting from the puncture wound which was just generated. Driven by the rotor 17 rotating in reverse (cf. FIG. 4), not only is the piercing drive 16 prepared for the next puncture by tensioning of the coiled spring 18, but rather also the holder 13 is again moved forward in the puncture direction (to the left in FIG. 7, in the x direction in FIG. 5). The guide cylinder 33 now travels down the second guide path 38. Its curved contour 41 causes the holder 13 to not only execute a movement parallel to the puncture axis (x axis), but rather simultaneously also a movement perpendicular to the puncture axis (in the y direction). Correspondingly, the test strip 30 is guided on a different movement path than the lancet 9 previously was to the piercing point. The dimension of the curved contour 41 in the y direction determines the amount of the transverse offset movement of the test strip 30 perpendicular to the puncture axis of the lancet 9.

Finally, the guide cylinder 33 reaches the position (4), which represents a second reversal point. If the movement direction of the holder 13 is again reversed from this position, the guide cylinder 33 now follows the linear section of the contour 41 of the second guide path 38 until the beginning of the transition path 42. The guide cylinder 33 subsequently "climbs" back "upward" to the first guide path 36 via the ramp of the transition path 42 and finally reaches the starting position (1) again.

The second guide path 38 is longer in the x direction than the first guide path 36. The movement path of the test strip 30 was thus longer than the movement path of the lancet 9. This is necessary because the test strip 30—in contrast to the rigid lancet 9—must be folded down together with the carrier band perpendicular to the puncture axis (downward in FIG. 5), in order to be pressed flatly on the puncture wound. The holder 13 was thus moved a significant distance further in the puncture direction during the second movement.

Figure 7:
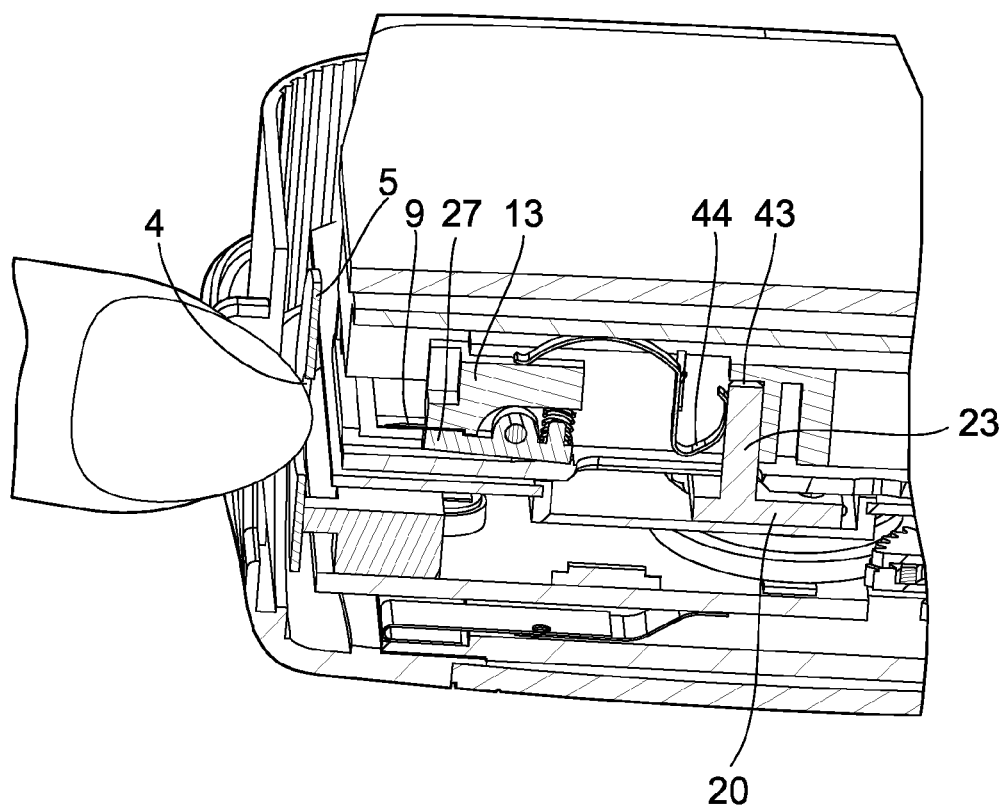
FIG. 7 is an enlarged vertical section through the front part of the apparatus of FIG. 1.

In the vertical section of FIG. 7, the puncture axis lies precisely in the plane of section. Therefore, only one half of the fixing ring 5 and half of the opening 4 are visible, through which a human finger protrudes a small amount. Only the half facing away from the observer is also visible of the holder 13. The clamping jaw 27 holds a lancet 9; the apparatus is thus prepared for a piercing. The coupling of the holder 13 on the sliding part 20 is well visible here, whose coupling pin 23 protrudes from below into the recess 43 of the holder 13 and is fixed by the leaf spring 44 so that the holder 13 can execute a limited tilting or pivot movement around the contact point between the curved part of the leaf spring 44 and the front side of the coupling pin 23 pointing in the puncture direction, in order to achieve the desired offset perpendicular to the puncture axis (upward in FIG. 7), when an analysis element is coupled on instead of the lancet 9. The holder 13 experiences a force downward via the leaf spring 44, which presses on top against the cover of the replaceable cassette, the force ensuring that the guide cylinders 33 are always in contact with the contours 39 and 40.

Figure 8:
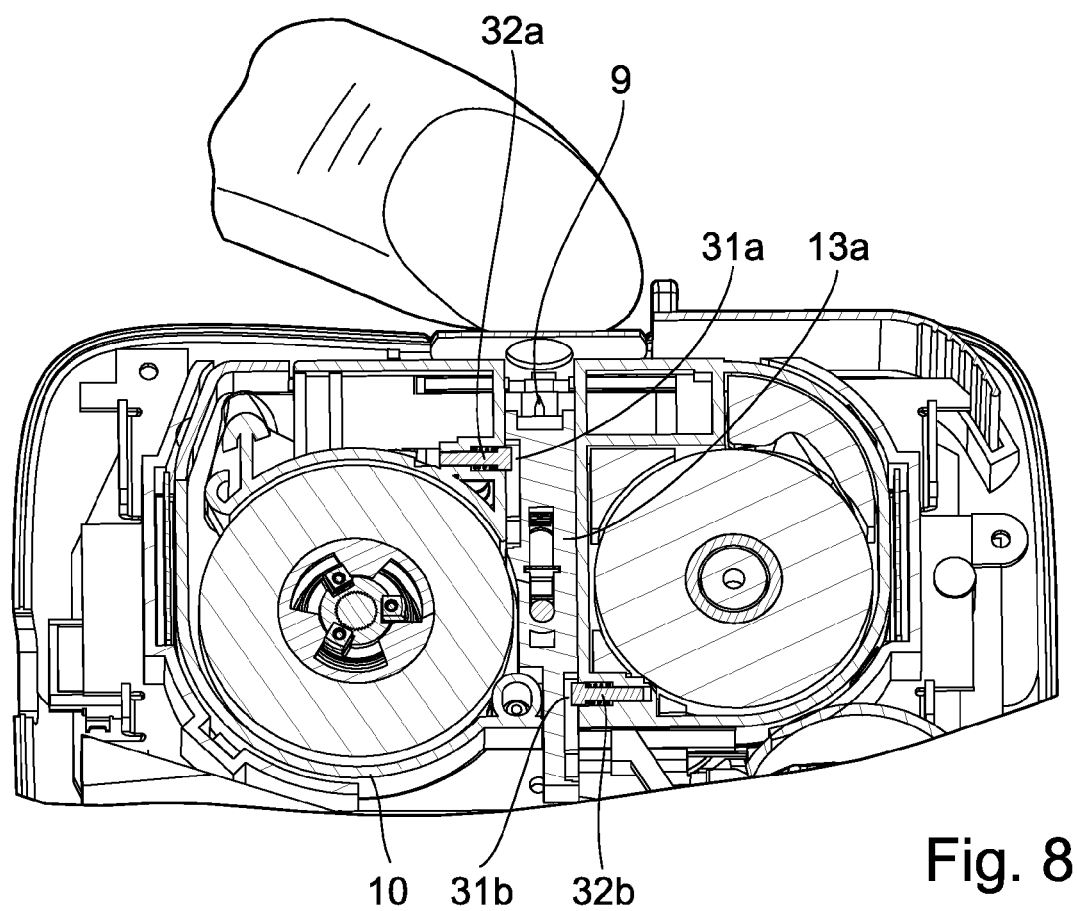
FIG. 8 is a sectional view of a replaceable cassette of an alternative embodiment of the apparatus.

The alternative embodiment of an apparatus for obtaining and analyzing a blood sample shown in FIG. 8 differs from the previously described apparatus in that the holder 13a is longer, so that its rear end protrudes out of the replaceable cassette 10. Control curves 31a and 31b implemented in mirror image are provided on the two long side walls of the holder 13a. In this embodiment the links are not directly opposite to one another here, but are rather located offset to one another along the puncture axis of the lancet 9 enough that they lie essentially one behind the other. The associated guide elements 32a, 32b are correspondingly located offset to one another by the same amount in the direction of the puncture axis. The configuration of the minor-image control curves 31a, 31b and the corresponding configuration of the associated guide elements 32a, 32b at the same height, but at different longitudinal positions of the holder 13a, has the advantage that the holder 13a can be raised or lowered as a whole via inclined contours inside the control curves 31a, 31b, without the holder 13a having to execute a pivot movement relative to the coupling pin 23 (cf. FIG. 7). In order to implement this lifting movement of the holder 13a parallel to the puncture axis with minimal force application, the friction between coupling pin 23 and plug receptacle 43 (cf. FIG. 7) is to be as low as possible.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS 1 housing
2 housing bottom part
3 housing cover
4 opening
5 fixing ring
6 operating panel
7 display
8 setting wheel
9 lancet
10 replaceable cassette
11 supply magazine
12 carrier band
13, 13a holder
14 electric motor
15 transfer gear
16 piercing drive
17 rotor
18 coiled spring
19 tappet pin
20 sliding part
21 recess
22 control curve
23 coupling pin
24 main body (of 13)
25 gripper
26 slot
27 clamping jaw 28 supply coil
29 winding coil
30 test strip
31, 31a, 31b control curves
32, 32a, 32b guide elements
33 guide cylinder
34 bearing journal
35 spring
36 first guide path
37 first plane
38 second guide path
39 second plane
40 linear contour
41 curved contour
42 transition path
43 plug receptacle
44 leaf spring

What is claimed is:

1. An apparatus for obtaining and analyzing a blood sample, comprising:
   a lancet configured for piercing the skin of a body part to produce a puncture wound;
   an analysis element configured to be guided to the body part to take up a blood sample exiting the puncture wound;
   a movably mounted holder to which the lancet and the analysis element can be coupled;
   a movement controller configured to guide the holder on a first movement path during which the lancet performs a puncture movement along a puncture axis and a second movement path during which the analysis element makes an offset movement transverse to the puncture axis;
   the movement controller comprising a three-dimensional guide slot having first and second guide paths which have different depths; and
   a guide element which travels along the guide slot.

2. The apparatus of claim 1, further comprising a housing and a fixing device provided on the housing, the fixing device configured for contacting a body part from which a blood sample is to be taken.

3. The apparatus of claim 1, further comprising a piercing drive configured to drive the holder to execute the movements of the lancet and the analysis element.

4. The apparatus of claim 1, wherein the first guide path comprises a contour that determines the first movement path and the second guide path comprises a contour that determines the second movement path.

5. The apparatus of claim 4, wherein the first guide path has a linear contour.

6. The apparatus of claim 4, wherein the second guide path has a curved contour, the curved contour causing the offset movement of the analysis element.

7. The apparatus of claim 1, wherein the guide slot comprises at least one ramp which connects the first guide path and the second guide path.

8. The apparatus of claim 1, wherein the guide slot is permanently connected to the holder and the guide element is fixed to a housing of the apparatus.

9. The apparatus of claim 1, wherein the guide element is maintained in engagement with the guide slot by a spring force.

10. The apparatus of claim 9, wherein the guide element comprises a guide cylinder which is mounted to allow axial displacement thereof.

11. The apparatus of claim 10, further comprising a spring which acts in the axial direction on the guide cylinder.

12. The apparatus of claim 1, wherein the guide element extends transversely to the puncture axis.

13. The apparatus of claim 12, wherein the guide slot comprises two mirror-image guide slots provided on two opposite side walls of the holder and the guide element comprises two guide elements, each of the two minor-image guide slots being engaged by a respective one of the two guide elements, the holder being mounted between the two guide elements.

14. The apparatus of claim 13, wherein the two minor-image guide slots are located diametrically opposite to one another.

15. The apparatus of claim 12, wherein the holder is connected to a piercing drive via an articulated coupling, thereby permitting a tilting movement of the holder around an axis perpendicular to the puncture axis.

16. The apparatus of claim 15, wherein the holder comprises a plug receptacle for a coupling pin of the piercing drive.

17. The apparatus of claim 16, further comprising a leaf spring, which presses from the side against the coupling pin and is seated in the plug receptacle.

18. The apparatus of claim 1, wherein the holder carries a clamping device on a front end thereof, the clamping device being configured to clamp on a lancet or a test strip.

19. The apparatus of claim 1, further comprising a removable cassette containing a supply of lancet and analysis elements.

20. The apparatus of claim 19, wherein the removable cassette contains a supply coil in which lancets and test strips are located on a carrier band, and a winding coil to take up used lancets and test strips.

21. The apparatus of claim 20, wherein the holder is mounted on the removable cassette.

22. The apparatus of claim 21, wherein the holder is located between the supply coil and the winding coil, whereby the carrier band is transported transversely to the puncture direction.

* * * * *

UNITED STATES PATENT AND TRADEMARK OFFICE
CERTIFICATE OF CORRECTION

PATENT NO. : 9,131,886 B2
APPLICATION NO. : 13/938000
DATED : September 15, 2015
INVENTOR(S) : Harttig et al.

Page 1 of 1

It is certified that error appears in the above-identified patent and that said Letters Patent is hereby corrected as shown below:

In The Claims

Claim 13, column 12, beginning on line 20, the phrase "two minor-image guide slots" is deleted and replaced with --two mirror-image guide slots--.

Claim 14, column 12, beginning on line 24, the phrase "two minor-image guide slots" is deleted and replaced with --two mirror-image guide slots--.

Signed and Sealed this
Twenty-sixth Day of January, 2016

Michelle K. Lee
*Director of the United States Patent and Trademark Office*